United States Patent
Bowdery (10) Patent No.: US 10,234,042 B2
(45) Date of Patent: Mar. 19, 2019

(54) DRAIN VALVE WITH ROTATABLE ANGLED OUTLET

(71) Applicant: Pall Corporation, Port Washington, NY (US)

(72) Inventor: Danniel Bowdery, Portsmouth (GB)

(73) Assignee: Pall Corporation, Port Washington, NY (US)

(*) Notice: Subject to any disclaimer, the term of this patent is extended or adjusted under 35 U.S.C. 154(b) by 0 days.

(21) Appl. No.: 15/610,901

(22) Filed: Jun. 1, 2017

(65) Prior Publication Data
US 2018/0347709 A1  Dec. 6, 2018

(51) Int. Cl.
| | |
|---|---|
| F16K 3/24 | (2006.01) |
| F16K 3/26 | (2006.01) |
| F16K 5/04 | (2006.01) |
| C12M 1/00 | (2006.01) |
| B01L 3/00 | (2006.01) |

(52) U.S. Cl.
CPC ............ *F16K 5/0407* (2013.01); *B01L 3/567* (2013.01); *C12M 29/00* (2013.01); *F16K 3/246* (2013.01); *F16K 3/265* (2013.01); *F16K 3/267* (2013.01); *F16K 5/0442* (2013.01); *B01L 2200/026* (2013.01); *B01L 2300/0858* (2013.01); *B01L 2400/0644* (2013.01)

(58) Field of Classification Search
CPC ... F16K 3/22; F16K 3/24; F16K 3/246; F16K 3/26; F16K 3/262; F16K 3/265; F16K 3/267; F16K 31/445; F16K 31/528; F16K 31/5286
See application file for complete search history.

(56) References Cited

U.S. PATENT DOCUMENTS

| | | | | |
|---|---|---|---|---|
| 3,684,240 A | * | 8/1972 | Stehlin | F16K 31/528 137/550 |
| 4,905,963 A | * | 3/1990 | Nichols | B67D 7/0294 251/144 |
| 5,435,339 A | * | 7/1995 | Hayes | F16K 31/528 137/315.04 |
| 6,341,762 B1 | * | 1/2002 | Dean | B64G 1/26 137/800 |
| 7,350,535 B2 | | 4/2008 | Liepold et al. | |
| 7,410,146 B2 | * | 8/2008 | Huang | F16K 3/265 251/144 |
| 7,614,607 B2 | | 11/2009 | Stiers | |
| 9,212,750 B2 | | 12/2015 | Blake et al. | |

(Continued)

FOREIGN PATENT DOCUMENTS

| | | |
|---|---|---|
| CA | 2278961 A1 | 1/2001 |
| CN | 105156689 A | 12/2015 |

(Continued)

OTHER PUBLICATIONS

Australian Patent Office, Examination Report in counterpart Australian Application No. 2018203721, dated Sep. 12, 2018.

(Continued)

*Primary Examiner* — Reinaldo Sanchez-Medina
*Assistant Examiner* — Hailey K Do
(74) *Attorney, Agent, or Firm* — Leydig Voit & Mayer (57) ABSTRACT

Drain valves with rotatable angled outlets that can be rotated without allowing flow or stopping flow through the valve, containers including the valves, and methods of using the valves, are disclosed.

12 Claims, 11 Drawing Sheets

(56) References Cited

U.S. PATENT DOCUMENTS

| | | |
|---|---|---|
| 2005/0016620 A1 | 1/2005 | Proulx et al. |
| 2006/0065587 A1 | 3/2006 | Shigesada et al. |
| 2008/0296217 A1 | 12/2008 | Thoraval et al. |
| 2010/0288691 A1 | 11/2010 | Shigesada et al. |
| 2011/0052102 A1 | 3/2011 | Stiers et al. |
| 2014/0026989 A1 | 1/2014 | Hillier et al. |
| 2017/0113912 A1 | 4/2017 | Johnson |
| 2017/0328506 A1 | 11/2017 | Chang |

FOREIGN PATENT DOCUMENTS

| | | | |
|---|---|---|---|
| DE | 202 04 658 U1 | 7/2003 | |
| EP | 1 632 698 A2 | 3/2006 | |
| EP | 2 060 835 A2 | 5/2009 | |
| EP | 2 889 080 A2 | 7/2015 | |
| GB | 601648 A * | 5/1948 | ............ F16K 3/265 |
| JP | 2004-330133 A | 11/2004 | |
| WO | WO 2014/009285 A1 | 1/2014 | |

OTHER PUBLICATIONS

Singaporean Patent Office, Search Report in counterpart Singaporean Application No. 10201802241P, dated Oct. 11, 2018.

European Patent Office, Extended European Search Report in counterpart European Application No. 18173922.8, dated Oct. 17, 2018.

* cited by examiner

DRAIN VALVE WITH ROTATABLE ANGLED OUTLET

BACKGROUND OF THE INVENTION

Drain valves for fluid product containers (such as liquid products used in the pharmaceutical and biotechnological industries) are known. However, there is a need for improved drain valves. The present invention provides for ameliorating at least some of the disadvantages of the prior art. These and other advantages of the present invention will be apparent from the description as set forth below.

BRIEF SUMMARY OF THE INVENTION

An embodiment of the invention provides a drain valve with a rotatable outlet comprising: (a) a hollow drain inlet comprising: (i) a hollow body having a first open end and a second open end, and an exterior surface, the exterior surface further comprising at least one outwardly extending lug, the first end further comprising a flange including a central opening having an internal diameter; (b) a valve member comprising closed first end and an open second end, (i) the closed first end having an external diameter and a side wall including at least two outwardly extending projections providing a circumferential channel therebetween, and a resilient ring arranged in the circumferential channel, (ii) a valve body having a base comprising the open second end, the second end having an external diameter and the valve body including at least one aperture, and a base side wall including a circumferential channel, wherein the external diameter of the closed first end is less than the external diameter of the second end and is at least equal to the internal diameter of the central opening of the flange, and, wherein the valve member is arranged within the hollow body of the hollow drain inlet and is axially moveable toward the first and second open ends of the hollow body within the hollow drain inlet; (c) the rotatable outlet comprising: (i) a hollow member having a first open end and a second open end, and an exterior surface, the exterior surface further comprising, arranged between the first open end and the second open end, at least two outwardly extending projections providing a circumferential channel therebetween, the hollow member forming an angle of at least about 20 degrees between the first end and the second end; and, (d) a rotatable collar comprising: (i) a shell body having a side wall having an internal surface including an inwardly projecting circumferential rib rotatably arranged in the circumferential channel of the rotatable outlet, the side wall further comprising at least one channel therethrough for receiving the outwardly extending lug of the drain inlet hollow body, the channel having corresponding channel walls, at least one terminal section including a closed end and a horizontal axis, and an angled section, angled from the horizontal axis; wherein rotating the rotatable collar moves the outwardly extending lug of the hollow body along the shell side wall channel such that the valve member can move axially toward the first end of the hollow drain inlet to a first position closing the central opening of the flange, preventing fluid flow therethrough, and the valve member can move axially toward the second end of the hollow drain inlet to a second position allowing fluid flow through the hollow drain inlet and the rotatable outlet; and wherein the rotatable outlet can be rotated independently of the rotatable collar without affecting the first position or the second position of the valve member.

An embodiment of a system for processing fluid comprises an embodiment of the drain valve with a rotatable outlet; and, a closed container having an interior volume suitable for containing fluid, the container comprising a bottom wall, a top wall, at least one side wall, the side wall(s) being joined to the top wall and the bottom wall; and at least an inlet port, and a drain valve, the drain valve being arranged in the bottom wall, wherein the hollow drain inlet flange of the drain valve is attached to the bottom wall of the container.

In another embodiment, a method of operating a drain valve is provided, the drain valve comprising (a) a hollow drain inlet comprising: (i) a hollow body having a first open end and a second open end, and an exterior surface, the exterior surface further comprising at least one outwardly extending lug, the first end further comprising a flange including a central opening having an internal diameter; (b) a valve member comprising closed first end and an open second end, (i) the closed first end having an external diameter and a side wall including at least two outwardly extending projections providing a circumferential channel therebetween, and a resilient ring arranged in the circumferential channel, (ii) a valve body having a base comprising the second end, the second end having an external diameter and the valve body including at least one aperture, and a base side wall including a circumferential channel, wherein the external diameter of the closed first end is less than the external diameter of the second end and is at least equal to the internal diameter of the central opening of the flange, and, wherein the valve member is arranged within the hollow body of the hollow drain inlet and is axially moveable toward the first and second open ends of the hollow body within the hollow drain inlet; (c) the rotatable outlet comprising: (i) a hollow member having a first open end and a second open end, and an exterior surface, the exterior surface further comprising, arranged between the first open end and the second open end, at least two outwardly extending projections providing a circumferential channel therebetween, the hollow member forming an angle of at least about 20 degrees between the first end and the second end; and, (d) a rotatable collar comprising: (i) a shell body having a side wall having an internal surface including an inwardly projecting circumferential rib rotatably arranged in the circumferential channel of the rotatable outlet, the side wall further comprising at least one channel therethrough for receiving the outwardly extending lug of the drain inlet hollow body, the channel having corresponding channel walls, at least one terminal section including a closed end and a horizontal axis, and an angled section, angled from the horizontal axis; wherein rotating the rotatable collar moves the outwardly extending lug of the hollow body along the shell side wall channel such that the valve member can move axially toward the first end of the hollow drain inlet to a first position closing the central opening of the flange, preventing fluid flow therethrough, and the valve member can move axially toward the second end of the hollow drain inlet to a second position allowing fluid flow through the hollow drain inlet and the rotatable outlet; and wherein the rotatable outlet can be rotated independently of the rotatable collar without affecting the first position or the second position of the valve member; the method comprising: rotating the rotatable collar and moving the outwardly extending lug of the hollow body along the shell side wall channel such that the valve member moves axially toward the first end of the hollow drain inlet to a first position closing the central opening of the flange, preventing fluid flow therethrough, and/or moving the valve member axially toward the second end of the hollow drain inlet to a second position allowing fluid flow through the hollow drain inlet and the rotatable outlet; the method optionally further including rotating the rotatable outlet independently of the rotatable collar.

BRIEF DESCRIPTION OF THE SEVERAL
VIEWS OF THE DRAWING(S)

FIGS. 10A (front perspective view), 10B (bottom isometric view), and 10C (side view) show various views of a system according to an embodiment of the invention, comprising a container and a drain valve mounted to a wall of the container.

DETAILED DESCRIPTION OF THE
INVENTION

A drain valve with a rotatable outlet according to an embodiment of the invention comprises (a) a hollow drain inlet comprising: (i) a hollow body having a first open end and a second open end, and an exterior surface, the exterior surface further comprising at least one outwardly extending lug, the first end further comprising a flange including a central opening having an internal diameter; (b) a valve member comprising closed first end and an open second end, (i) the closed first end having an external diameter and a side wall including at least two outwardly extending projections providing a circumferential channel therebetween, and a resilient ring arranged in the circumferential channel, (ii) a valve body having a base comprising the open second end, the second end having an external diameter and the valve body including at least one aperture, and a base side wall including a circumferential channel, wherein the external diameter of the closed first end is less than the external diameter of the second end and is at least equal to the internal diameter of the central opening of the flange, and, wherein the valve member is arranged within the hollow body of the hollow drain inlet and is axially moveable toward the first and second open ends of the hollow body within the hollow drain inlet; (c) the rotatable outlet comprising: (i) a hollow member having a first open end and a second open end, and an exterior surface, the exterior surface further comprising, arranged between the first open end and the second open end, at least two outwardly extending projections providing a circumferential channel therebetween, the hollow member forming an angle of at least about 20 degrees between the first end and the second end; and, (d) a rotatable collar comprising: (i) a shell body having a side wall having an internal surface including an inwardly projecting circumferential rib rotatably arranged in the circumferential channel of the rotatable outlet, the side wall further comprising at least one channel therethrough for receiving the outwardly extending lug of the drain inlet hollow body, the channel having corresponding channel walls, at least one terminal section including a closed end and a horizontal axis, and an angled section, angled from the horizontal axis; wherein rotating the rotatable collar moves the outwardly extending lug of the hollow body along the shell side wall channel such that the valve member can move axially toward the first end of the hollow drain inlet to a first position closing the central opening of the flange, preventing fluid flow therethrough, and the valve member can move axially toward the second end of the hollow drain inlet to a second position allowing fluid flow through the hollow drain inlet and the rotatable outlet; and wherein the rotatable outlet can be rotated independently of the rotatable collar without affecting the first position or the second position of the valve member.

In an embodiment, the at least one terminal section of the shell body side wall channel includes a lug retaining section having a cross-sectional area narrower than an outer diameter of the lug, the lug retaining section providing resistance as the lug passes through the narrower cross-sectional area. In a more preferred embodiment, the at least one channel in the shell body side wall has two terminal sections, each including a closed end and a horizontal axis, and the angled section, angled from the horizontal axis, is arranged between the two terminal sections, the two terminal sections each including a lug retaining section having a cross-sectional area narrower than an outer diameter of the lug, the lug retaining section providing resistance as the lug passes through the narrower cross-sectional area.

In an embodiment, the closed first end of the valve member has a dome shape.

In some embodiments, the valve body and the rotatable body are an integral unit.

An embodiment of a system for processing fluid comprises an embodiment of the drain valve with a rotatable outlet; and, a closed container having an interior volume suitable for containing fluid, the container comprising a bottom wall, a top wall, at least one side wall, the side wall(s) being joined to the top wall and the bottom wall; and at least an inlet port, and a drain valve, the drain valve being arranged in the bottom wall, wherein the hollow drain inlet flange of the drain valve is attached to the bottom wall of the container.

In another embodiment, a method of operating a drain valve is provided, the drain valve comprising (a) a hollow drain inlet comprising: (i) a hollow body having a first open end and a second open end, and an exterior surface, the exterior surface further comprising at least one outwardly extending lug, the first end further comprising a flange including a central opening having an internal diameter; (b) a valve member comprising closed first end and an open second end, (i) the closed first end having an external diameter and a side wall including at least two outwardly extending projections providing a circumferential channel therebetween, and a resilient ring arranged in the circumferential channel, (ii) a valve body having a base comprising the open second end, the second end having an external diameter and the valve body including at least one aperture, and a base side wall including a circumferential channel, wherein the external diameter of the closed first end is less than the external diameter of the second end and is at least equal to the internal diameter of the central opening of the flange, and, wherein the valve member is arranged within the hollow body of the hollow drain inlet and is axially moveable toward the first and second open ends of the hollow body within the hollow drain inlet; (c) the rotatable outlet comprising: (i) a hollow member having a first open end and a second open end, and an exterior surface, the exterior surface further comprising, arranged between the first open end and the second open end, at least two outwardly extending projections providing a circumferential channel therebetween, the hollow member forming an angle of at least about 20 degrees between the first end and the second end; and, (d) a rotatable collar comprising: (i) a shell body having a side wall having an internal surface including an inwardly projecting circumferential rib rotatably arranged in the circumferential channel of the rotatable outlet, the side wall further comprising at least one channel therethrough for receiving the outwardly extending lug of the drain inlet hollow body, the channel having corresponding channel walls, at least one terminal section including a closed end and a horizontal axis, and an angled section, angled from the horizontal axis; wherein rotating the rotatable collar moves the outwardly extending lug of the hollow body along the shell side wall channel such that the valve member can move axially toward the first end of the hollow drain inlet to a first position closing the central opening of the flange, preventing fluid flow therethrough, and the valve member can move axially toward the second end of the hollow drain inlet to a second position allowing fluid flow through the hollow drain inlet and the rotatable outlet; and wherein the rotatable outlet can be rotated independently of the rotatable collar without affecting the first position or the second position of the valve member; the method comprising: rotating the rotatable collar and moving the outwardly extending lug of the hollow body along the shell side wall channel such that the valve member moves axially toward the first end of the hollow drain inlet to a first position closing the central opening of the flange, preventing fluid flow therethrough, and/or moving the valve member axially toward the second end of the hollow drain inlet to a second position allowing fluid flow through the hollow drain inlet and the rotatable outlet; the method optionally further including rotating the rotatable outlet independently of the rotatable collar.

Advantageously, in contrast with conventional drain valves, wherein the outlet is fixed in one orientation, possibly requiring the use of additional tubing and/or additional components to provide suitable fluid drainage, the use of a drain valve with a rotatable angled outlet allows tubing to be easily routed to the correct position without additional tubing and/or components. Additionally, in some situations, connecting the additional tubing and/or components creates the possibilities of leaks, which can be avoided using the drain valve with a rotatable angled outlet.

Furthermore, the use of a drain valve with a rotatable angled outlet can reduce the possibility of kinks and/or tight bends in tubing, while providing fast drain times.

Embodiments of the invention are particularly suitable for single-use systems such as single-use bioreactor bags.

A variety of fluids, especially liquids, can be processed and/or prepared (including mixing) in accordance with embodiments of the invention. The preparation of fluids, particularly solutions and suspensions in the pharmaceutical and biopharmaceutical industries, typically involves thorough mixing to provide the desired distribution of ingredients in the product. Applications for embodiments of the invention include, for example, cell culture (e.g., including batch and fed-batch operations of suspension and adherent cell lines), preparing sterile fluids for the pharmaceutical and/or biopharmaceutical industries, including drugs, vaccines, and intravenous fluids, antibody- and/or protein-containing fluids, and/or fluids for the food and beverage industry. Fluids processed and/or prepared according to embodiments of the invention can also be used, for example, as media and/or buffers such as chromatography buffers.

Each of the components of the invention will now be described in more detail below, wherein like components have like reference numbers.

FIGS. 1-8, particularly FIGS. 1, 3, and 6-8, show an illustrative embodiments of a drain valve 1000 comprising a hollow drain inlet 100, a valve member 200, a rotatable outlet 300, and a rotatable collar 400. As will be explained in more detail below, upon rotating the rotatable collar 400, the valve member 200 is axially movable up and down in the valve between a first position 1 preventing fluid flow through the valve, and a second position 2 allowing fluid flow through the valve, and the rotatable outlet 300 can be rotated (as reflected by arrow "A," e.g., perpendicularly to the axial movement of the valve member 200), without affecting the first position or the second position of the valve member. Put another way, when the valve member is in the first position, rotating the rotatable outlet will not result in liquid passing through the valve, and when the valve is in the second position, rotating the rotatable outlet will not result in preventing liquid from passing through the valve.

In the Figures, the illustrated hollow drain inlet 100 comprises a hollow body 140 having a first open end 101, a second open end 102, and a central lumen 105, the body having an external surface 120 including one or more lugs 125, the lugs having an outer diameter 125a. The first open end 101 further comprises a flange 150 having an upper surface 151 (e.g., that contacts fluid) and a lower surface 152 (e.g., for mounting to an inner surface of a wall of a container), the flange including a central opening 155 having an internal diameter 155a providing the first open end 101. The flange 150 is illustrated (in an embodiment of a system including the drain valve as illustrated in FIG. 10) as having an upper surface essentially flush with a wall of the container, for efficient mixing and/or reducing container hold up volume.

The illustrated valve member 200 comprises a first closed end 201 and a second open end 202. The first closed end has a top surface 251, illustrated as having a domed shape (e.g., to reduce media (e.g., powder) settling when the container is being drained and/or media is being mixed), the first closed end having an external diameter 225 and side wall 210 including outwardly extending projections 211a, 211b, providing a circumferential channel 212 therebetween, wherein a resilient ring 213 is arranged in the channel 212. The illustrated valve member 200 has a valve body 230 having a base 250 having an upper surface 251, the base 250 including the second open end 202, wherein the second open end has an external diameter 245, and a side wall 240, wherein the side wall 240 includes a circumferential channel 242, wherein a resilient ring 243 is arranged in the channel 242. The valve body 230 includes at least one aperture, in the illustrated embodiment, side cut-outs 231a, 231b, communicating with the opening 202a in the second end 202.

As will be discussed in more detail below, in the embodiment shown in FIGS. 1, 3, and 5, the valve body 230 of the valve member 200 is integral with the rotatable outlet 300 to provide a movable integral unit 500 (and the resilient rings 213 and 243 can be subsequently arranged in the channels 212 and 242).

Figure 6:
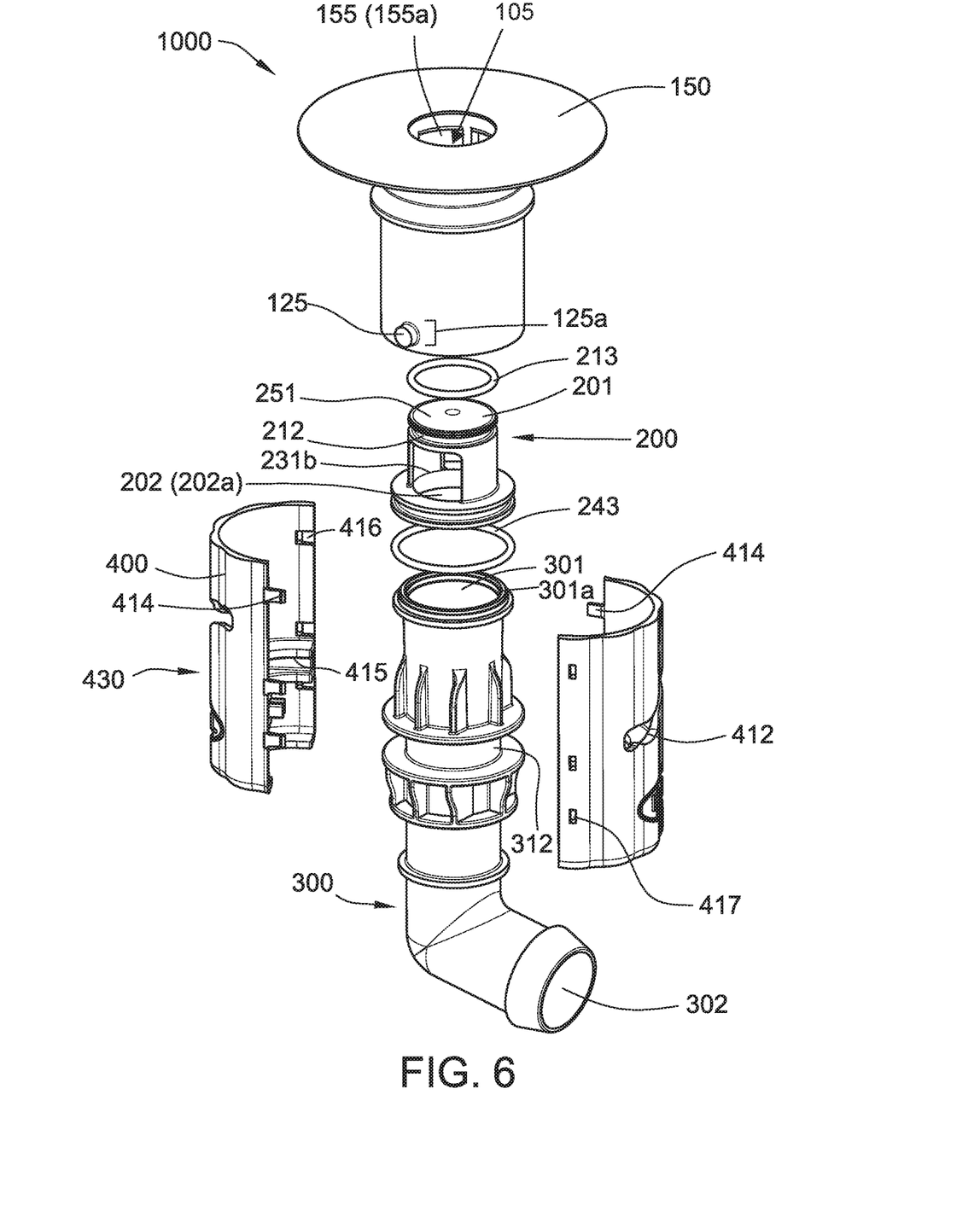
FIG. 6 is an isometric exploded view of a drain valve including an angled rotatable outlet and a valve member according to another embodiment of the present invention.
Figure 7:
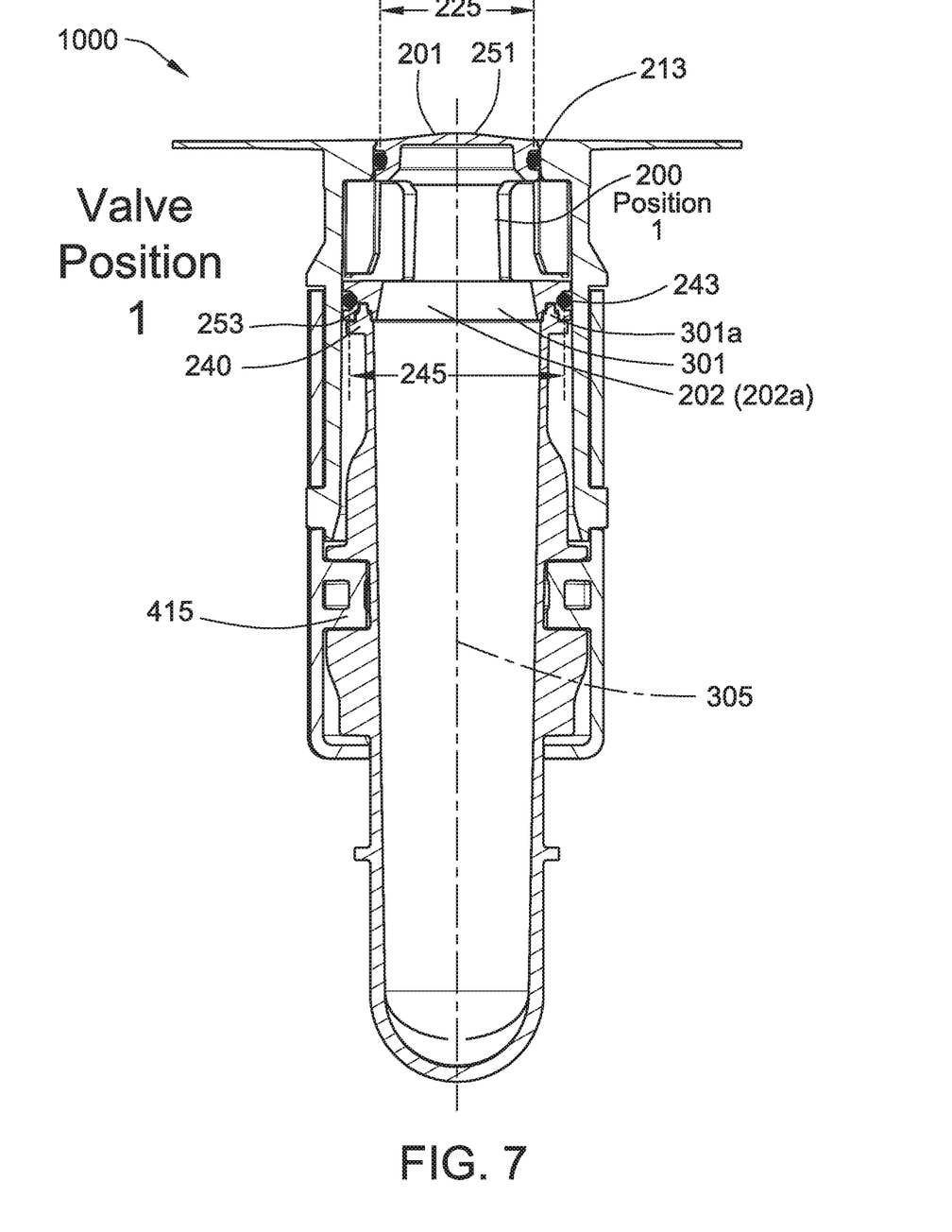
FIG. 7 is a cross-sectional view of the embodiment of the drain valve shown in FIG. 6, wherein the valve is in the closed position.
Figure 8:
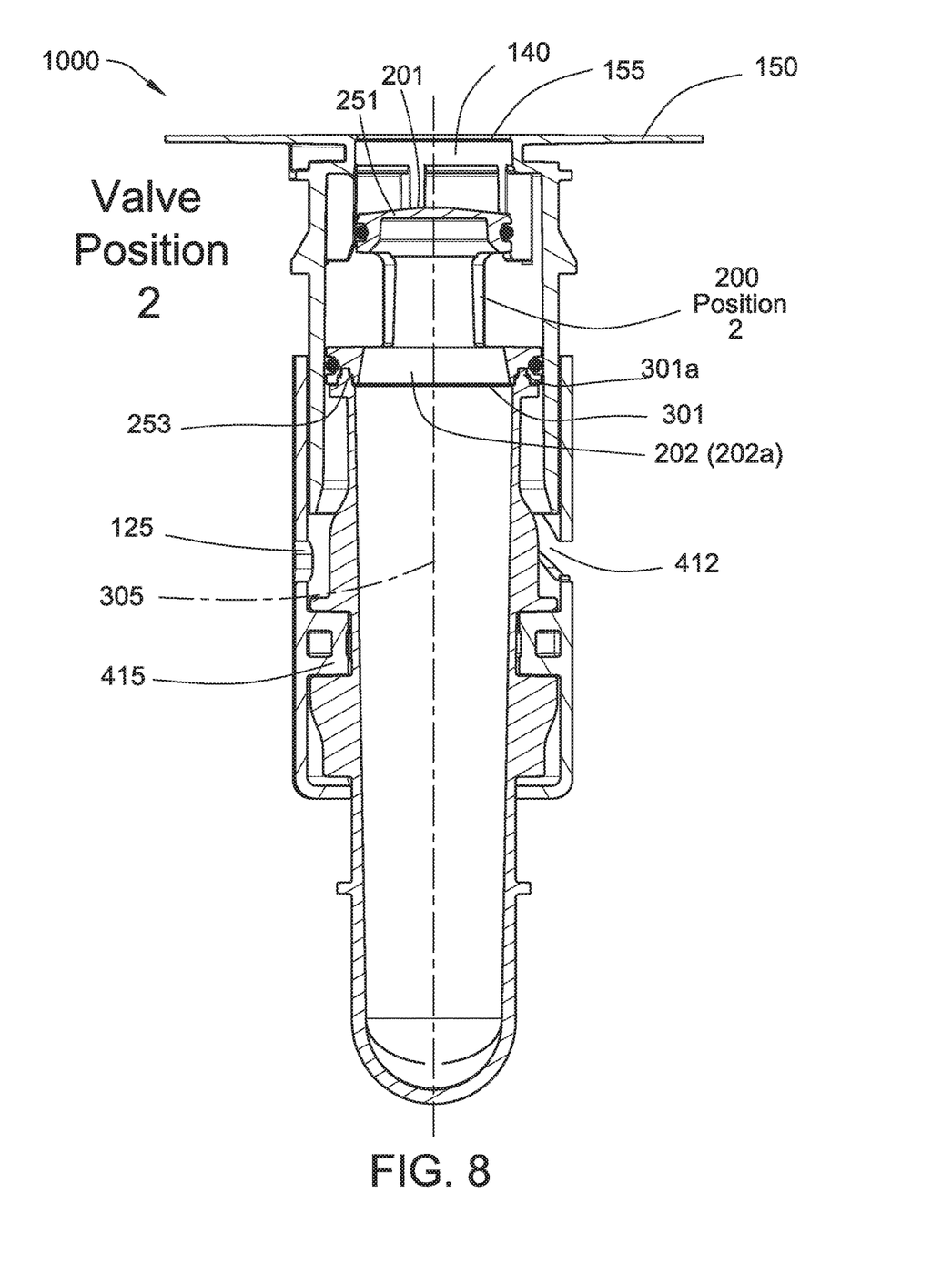
FIG. 8 is a cross-sectional view of the embodiment of the drain valve shown in FIG. 6, wherein the valve is in the open position.

Alternatively, as shown in FIGS. 6-8, valve member 200 can have a lower surface 252 further comprising a groove 253, arranged to receive a lip 301a (of the rotatable outlet 300), arranged to securely fit within the groove 253 of the base 250 of the valve body 230 such that the valve member moves with the outlet, wherein valve member 200 is not integral with rotatable outlet 300.

The external diameter 225 (of the first end 201) is less than the external diameter 245 (of the second end 202) and is at least equal to, and in some embodiments, larger than, the internal diameter 155a of the hollow drain inlet 100. The size of the external diameter 225 is sufficient to seal the internal diameter 155a and prevent liquid flow therethrough.

In use, the valve member 200 is arranged in the central lumen 105 of the hollow drain inlet, and is axially moveable in the valve 1000 between the first position 1 and the second position 2.

The illustrated rotatable outlet 300 comprises a hollow member 320 having a first open end 301 and a second open end 302, with a central lumen 305, and an external surface 310 including, arranged between ends 301 and 302, outwardly extending projections 311a, 311a, providing a circumferential channel 312 therebetween. The hollow member forms an angle of at least about 20 degrees between the first and second ends, and, while it can include any suitable angle, is illustrated as having an angle of about 100 degrees.

If desired, the outlet can include, for example, outwardly extending vertical projections 320a, 320b, preferably, wherein an end of the projections contacts projections 311a and 311b, e.g., to provide strength for the outwardly extending projections 311a and 311b and/or ensure that the rotatable collar is assembled in the correct position on the drain valve.

Figure 1:
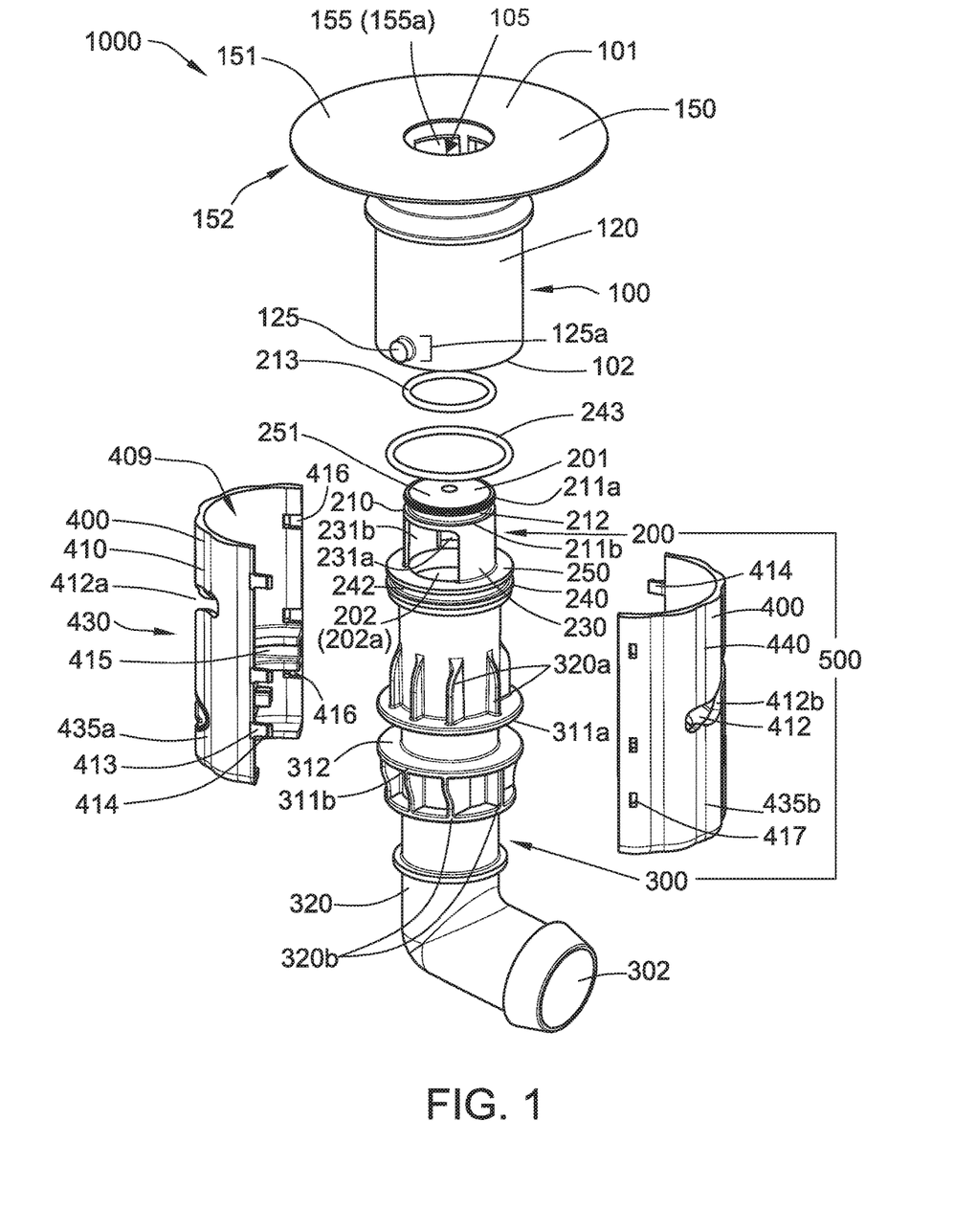
FIG. 1 is an isometric exploded view of a drain valve including an angled rotatable outlet and a valve member according to an embodiment of the present invention, wherein the outlet is integral with the valve member.
Figure 2:
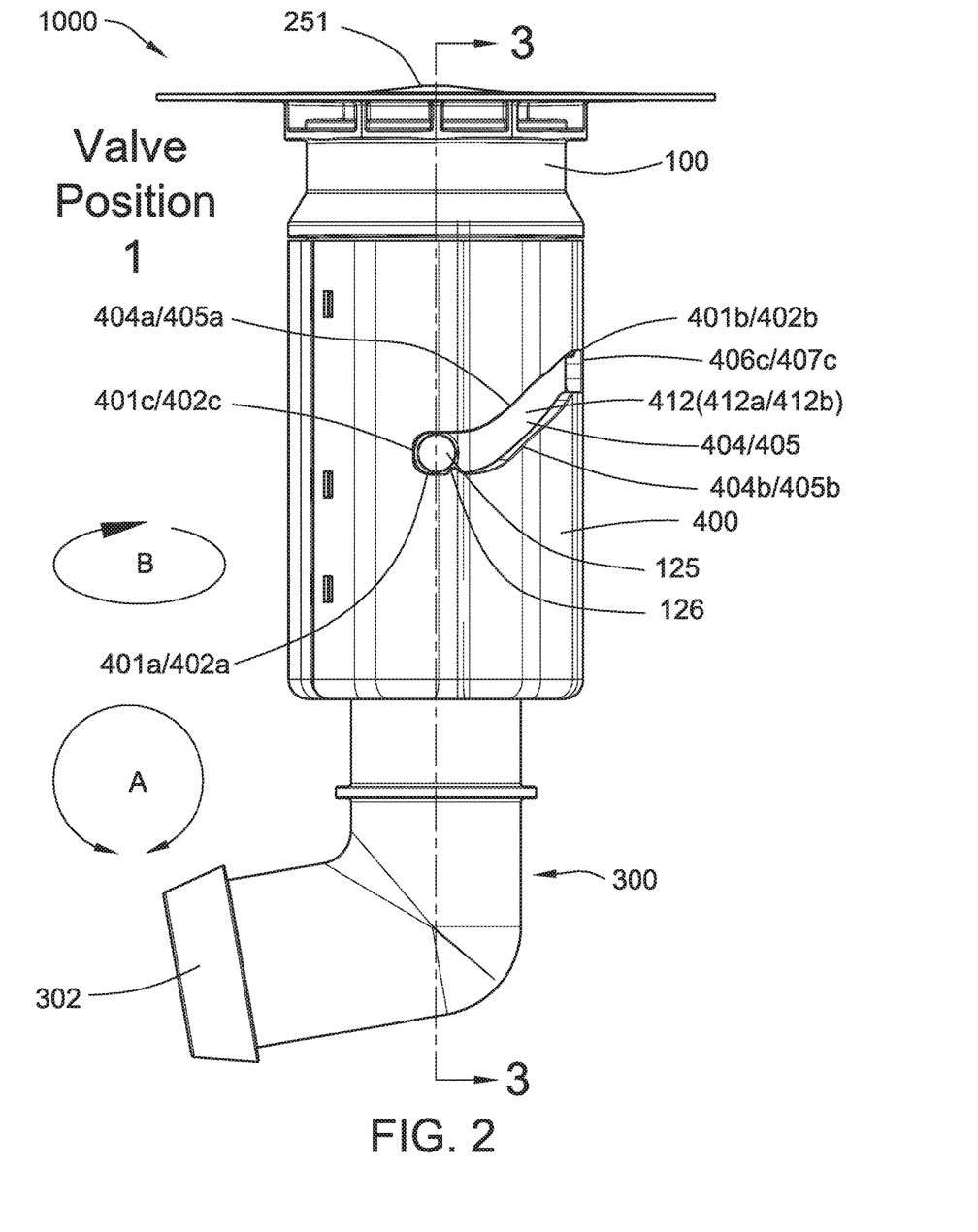
FIG. 2 is a side view of the embodiment of the drain valve shown in FIG. 1, also showing a channel and a locking lug, wherein the valve is in a closed position.
Figure 3:
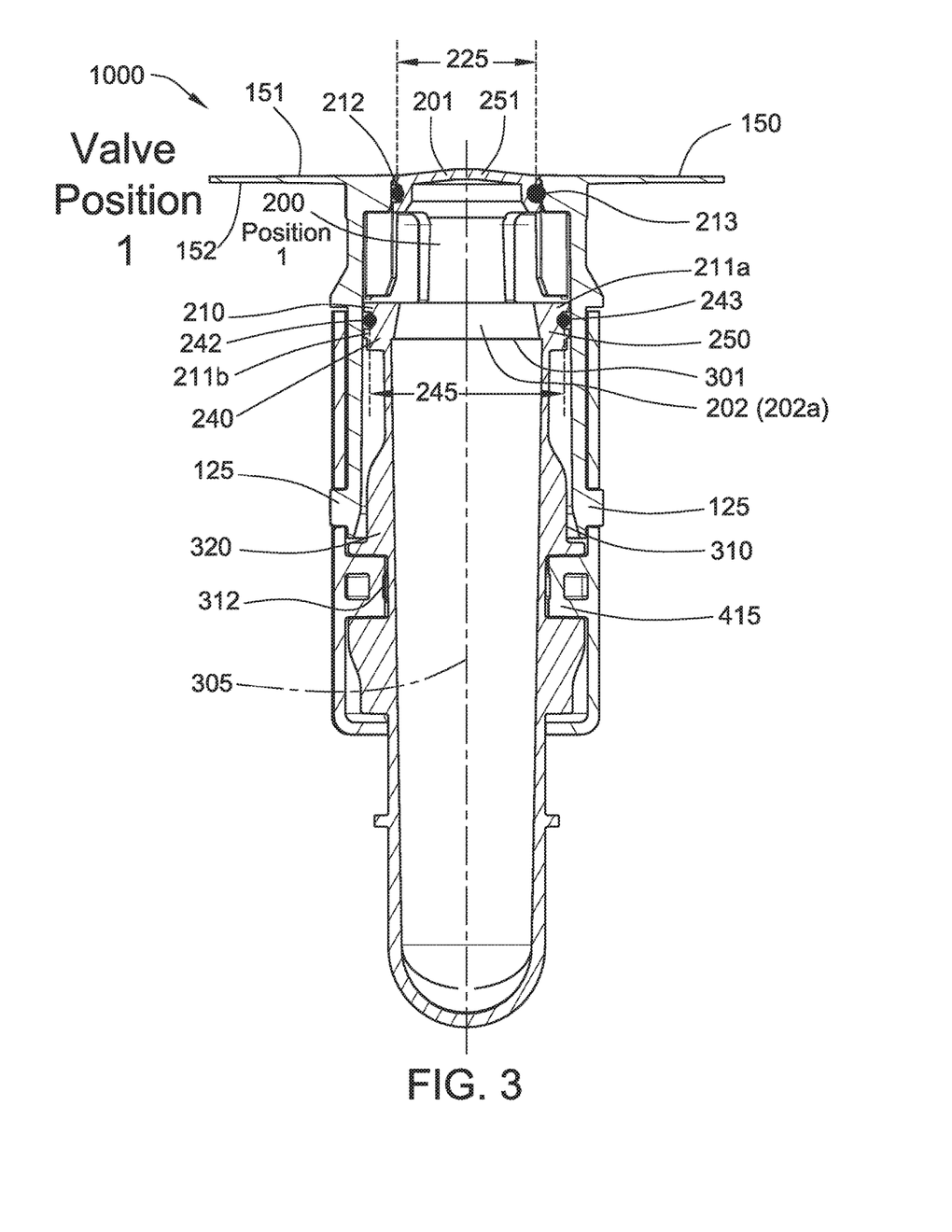
FIG. 3 is a cross-sectional view of the embodiment of the drain valve shown in FIG. 1, wherein the valve is in the closed position.
Figure 4:
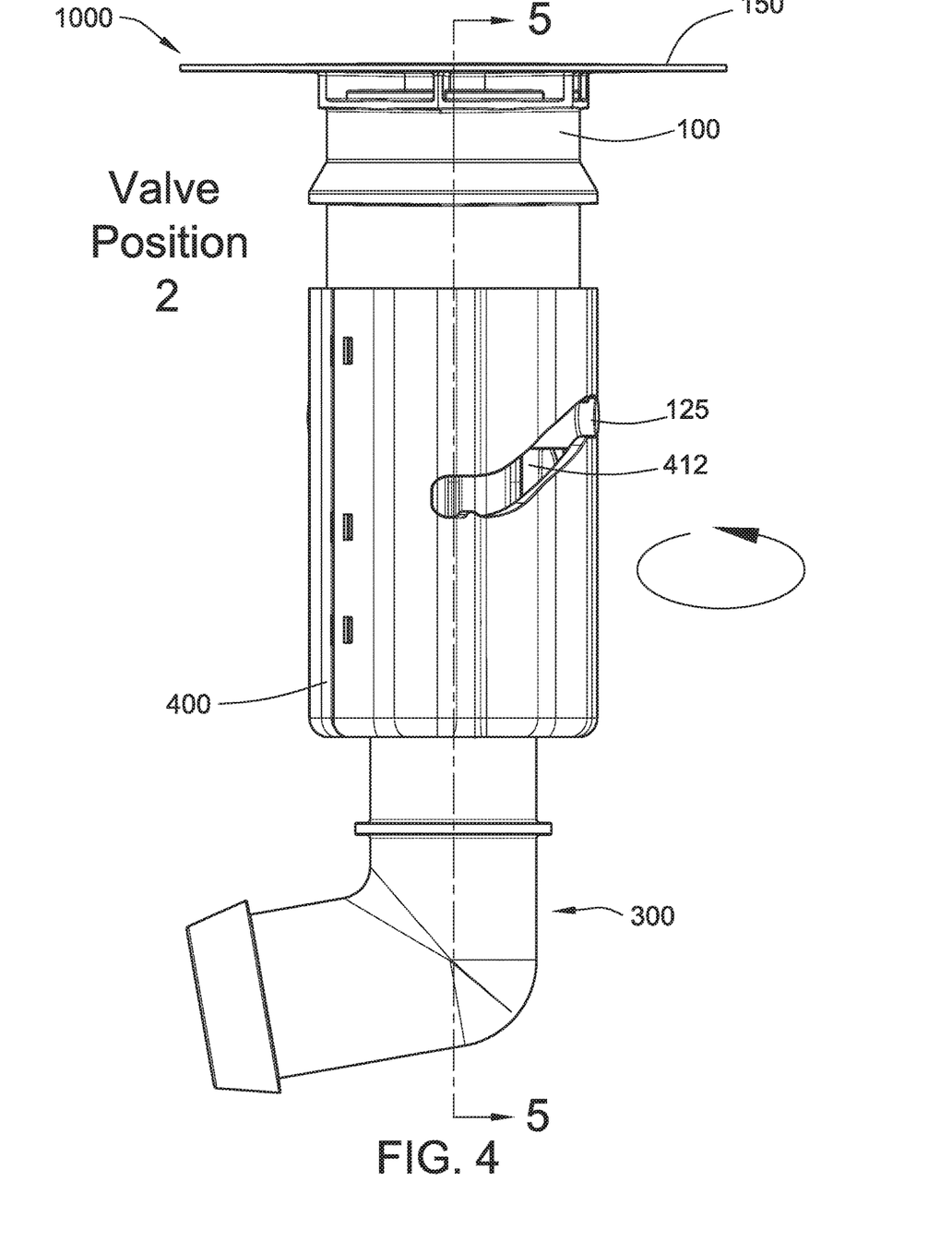
FIG. 4 is a side view of the embodiment of the drain valve shown in FIG. 1, also showing a channel and a locking lug, wherein the valve is in an open position.
Figure 5:
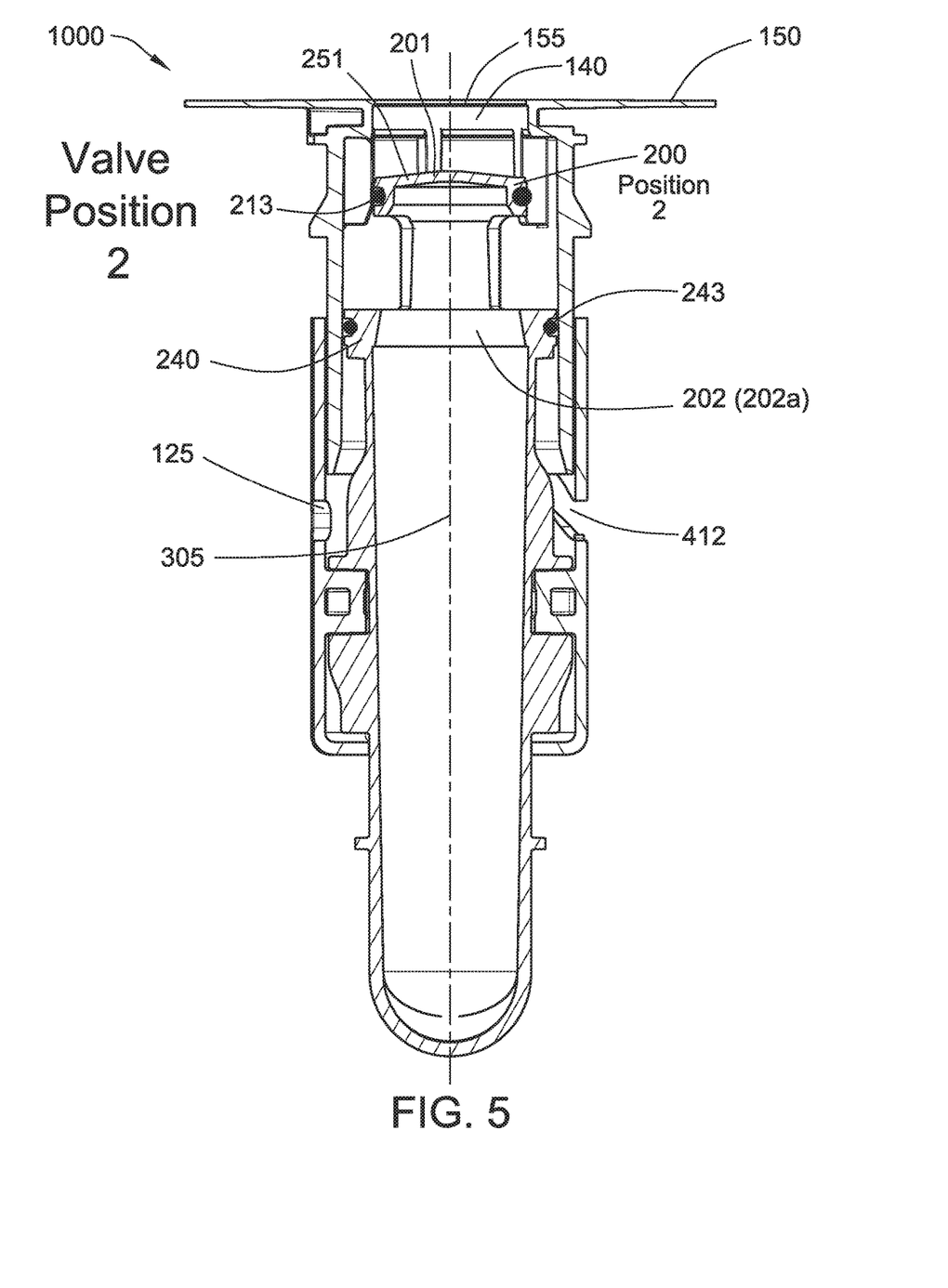
FIG. 5 is a cross-sectional view of the embodiment of the drain valve shown in FIG. 1, wherein the valve is in the open position.

If desired, e.g., as shown in FIGS. 1, 3, and 5, the valve member 200 is integral with the rotatable outlet 300 to provide a movable integral unit 500, such that when the valve member axially moves between the first position 1 and the second position 2, the outlet also moves axially between the positions. Illustratively, the valve member and rotatable outlet can be injection molded as a single integral unit.

Alternatively, as shown in FIGS. 6-8, the first open end 301 further includes a lip 301a, arranged to securely fit within the groove 253 of the base 250 of the valve body 230, such that when the valve member axially moves between the first position 1 and the second position 2, the outlet also moves axially between the positions.

The illustrated rotatable collar 400 comprises a shell body 430 having a side wall 440. Preferably, the shell body comprises sections that are assembled to provide the shell body, and in the illustrated embodiment, sections 435a and 435b are engaged to form the shell body. If desired (e.g., to reduce manufacturing costs), the sections can be identical.

The sections 435a and 435b can have a variety of configurations for engagement together as are known in the art. In the illustrated embodiments (see, for example, FIGS. 9A-9D), the sections have fingers 413 with lips 414 (e.g., along one part of a given section) that engage with respective slots 416 and holes 417 (e.g., along one part of the other section).

The shell body side wall 440 includes an internal surface 409 and an external surface 410, and at least one channel 412 passing through the side wall for receiving the outwardly extending lug 125 of the drain inlet hollow body, wherein a drain inlet lug is movable within the channel. In the illustrated embodiments, the side wall 440 includes two channels, 412a, 412b (section 435a includes channel 412a and section 435b includes channel 412b), wherein drain inlet lugs 125 are movable within the respective channels.

The internal surface 409 of the side wall 440 includes an inwardly projecting circumferential rib 415 rotatably arranged in the circumferential channel 312 of the rotatable outlet. Typically, the circumferential rib 415 is dimensioned (e.g., with respect to height and/or width) to substantially fill the circumferential channel 312 when the collar is assembled on the valve member/rotatable outlet. In the illustrated embodiments each section 435a, 435b includes a section of the circumferential rib 415, each section of the circumferential rib 415 having pins and an opening, wherein the pins in one section of the rib fit into the opening in the other section of the rib (see, for example, FIGS. 9C-9D).

The illustrated channels 412a, 412b each have corresponding channel walls, at least one terminal section including a closed end and a horizontal axis, and an angled section, angled from the horizontal axis. In some embodiments (see, for example, FIGS. 2, 9A, and 9B), each channel can have a first terminal section 401a,402a having a closed end 401c,402c and a second terminal section 401b,402b having a closed end 406c,407c, with the angled section 404,405 between the terminal sections. In the illustrated embodiment (see, for example, FIGS. 2, 9A, and 9B), the walls 404a, 405a; 404b,405b of the angled section 404,405 of the channels are generally parallel to each other, and the walls 401d,402d; 401e,402e (terminal sections 401c,402c) and side walls 401f,402f; 401g,402g (terminal section 406c, 407c) are general parallel to each other. The angled section can be provided as any suitable angle, e.g., from about 20°/160° to about 40°/120° from the horizontal axis, and other angles are suitable.

If desired, the collar can be adapted for further ease of use by the operator. For example external surface 410 can have a knurled surface for ease of grip and rotation by the operator.

In use, the operator's rotation of the rotatable collar 400 allows the outwardly extending lug 125 of the hollow body to move along the shell side wall channel such that the valve member 200 can move axially toward the first end 101 of the hollow drain inlet to a first position 1 closing the central opening of the flange, preventing fluid flow therethrough, and the valve member 200 can move axially toward the second end 102 of the hollow drain inlet to a second position 2 (upon rotating the collar 400 in the direction "B" shown in FIG. 2) allowing fluid flow through the hollow drain inlet and the rotatable outlet (wherein the rotatable outlet 300 moves axially with the valve member 200 from one position to the other); and, since the inwardly projecting circumferential rib 415 of the rotatable collar 400 is rotatably arranged in the circumferential channel 312 of the rotatable outlet 300, the rotatable outlet 300 can be rotated (e.g., 360 degrees) independently of the rotatable collar 400 without affecting the first position or the second position of the valve member.

Figure 9A:
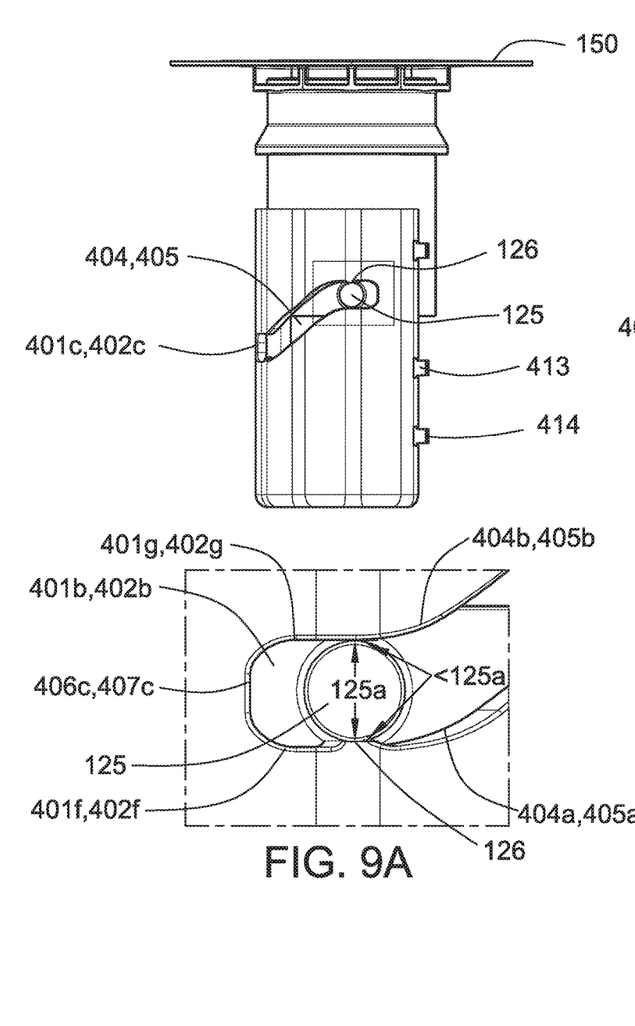
FIGS. 9A and 9B show enlarged views of a terminal section of the channel and the locking lug, also showing a locking lug retainer at one end of the channel, also showing the lug contacting the retainer as the rotatable collar begins to rotate from the position shown in FIG. 9A to the position shown in FIG. 9B.
Figure 9B:
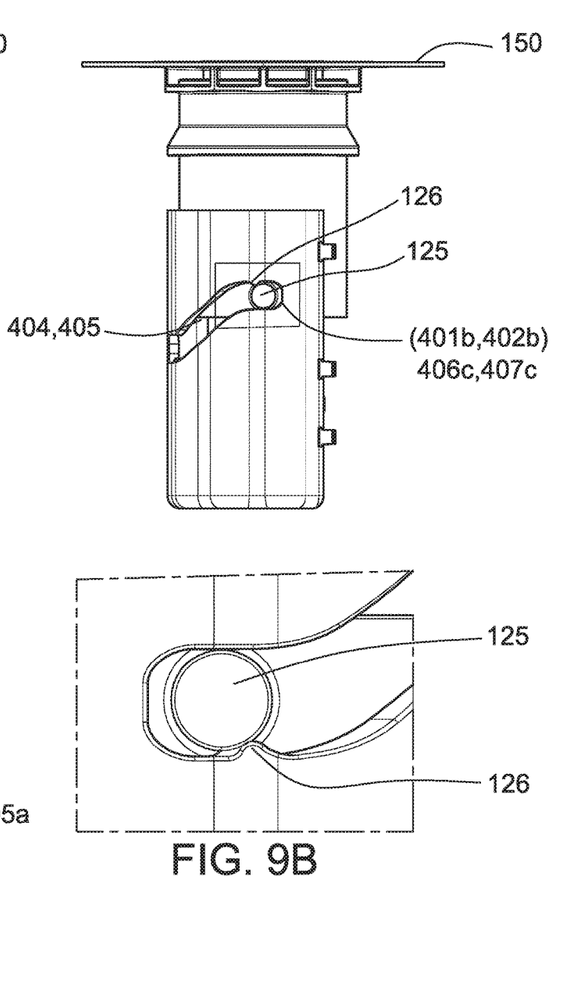
Figure 9C:
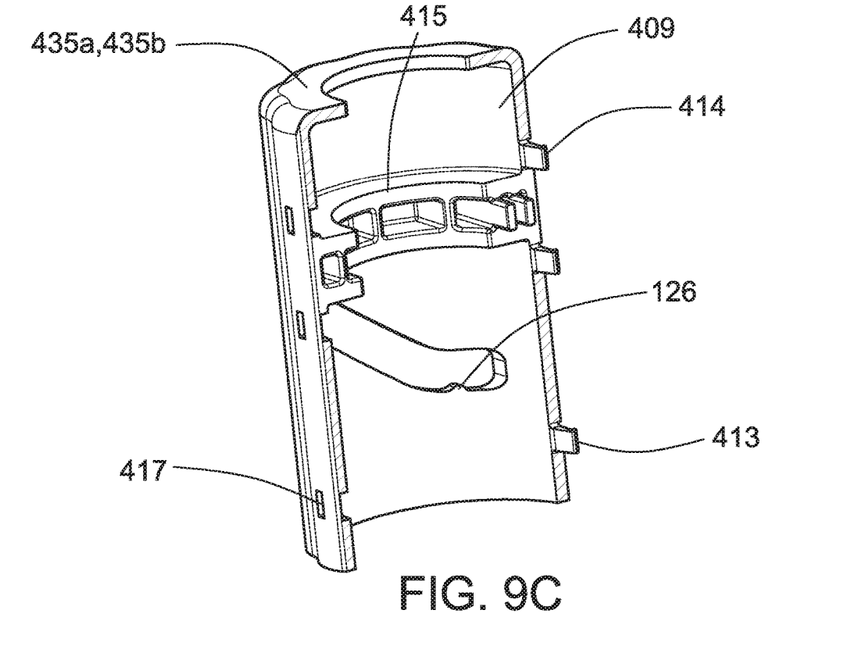
FIGS. 9C and 9D show isometric views of the interior of the rotatable collar of the embodiment of the drain valve shown in FIG. 1.
Figure 9D:
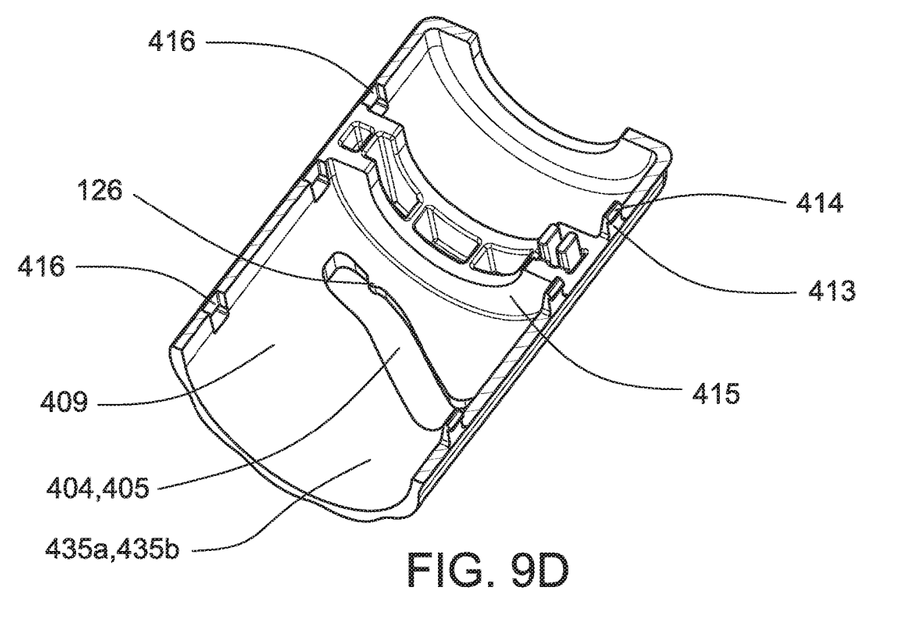

If desired, e.g., in order to provide the operator with tactile feedback and/or to reduce accidental operation (opening/closing) of the drain valve, the terminal section(s) of the shell body side wall channel can each include a lug retaining section 126 having a cross-sectional area narrower than an outer diameter 125a of the lug 125, the lug retaining section providing resistance as the lug passes through the narrower cross-sectional area (see, FIGS. 9A and 9B). The operator can recognize the change in resistance when the lug passes from the angled section of the channel to the terminal (or to either terminal) section of the channel. Additionally, since the distance between the corresponding walls of the channel at the lug retaining section is narrower than the outer diameter 125a of the lug, the lug is prevented from easily rotating out of the terminal section(s).

If desired, the drain valve can be provided assembled, or in kit form. For example, the integral unit 500 (with resilient rings 213 and 243 arranged in the channels), sections 435a and 435b, the drain inlet 100 including the flange 150, can be obtained, preferably in a clean room, placed in double bags, and sterilized (e.g., by gamma irradiation). Subsequently, the components can be assembled and attached to a container.

A variety of materials are suitable for the components of the valve and are known to one of skill in the art. Preferably, those materials that will be in contact with the fluid being processed are free of bisphenol A (BPA), for example, polyester (PES) (for example, injection moulded PESs such as polyethylene butylene terephthalate (PBT), polycarbonate (PC), and polysulfone (PSU)), soft rubbers, thermoplastic elastomers (TPEs), silicone (e.g., silicone 8701) (for example, soft rubbers, TPEs, and silicones having a shore A hardness of about 65 to about 75), and high density plastic (e.g., a high density injection moulded plastic such as high density polyethylene (HDPE)).

In those embodiments wherein the drain valve is joined to a plastic bag film, the flange is preferably formed from a high density injection moulded plastic (such as high density polyethylene (HDPE)) suitable for joining to the plastic film.

Embodiments of the invention are suitable for use with a variety of containers having any suitable volume, and are particularly suitable for flexible (e.g., plastic) containers having internal volumes of at least about 500 L.

In another embodiment, a system is provided, comprising a container (such as a biocontainer or a bioprocessing container) and a drain valve, attached to a wall of the container.

Figures 10A, 10B:
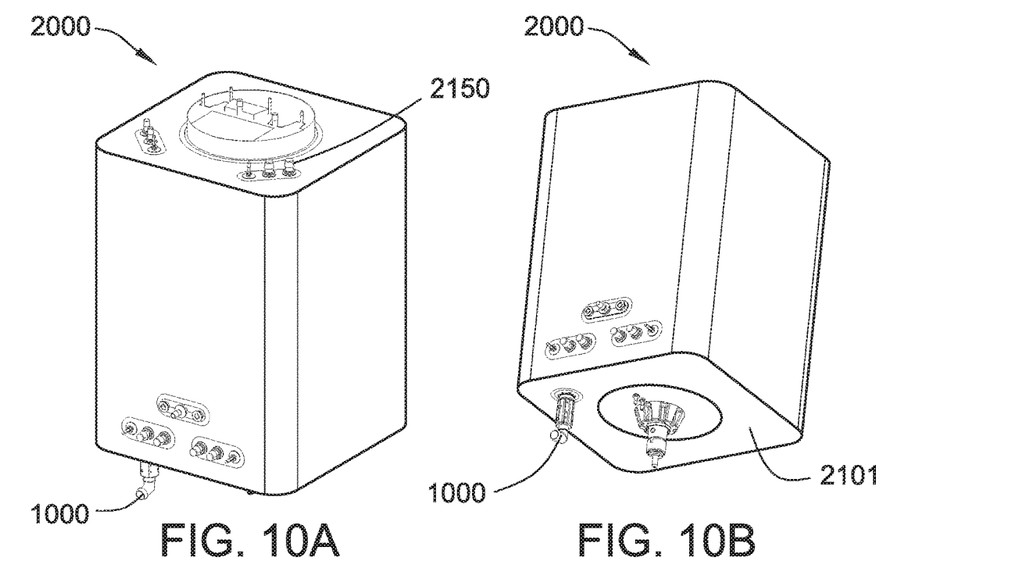
Figure 10C:
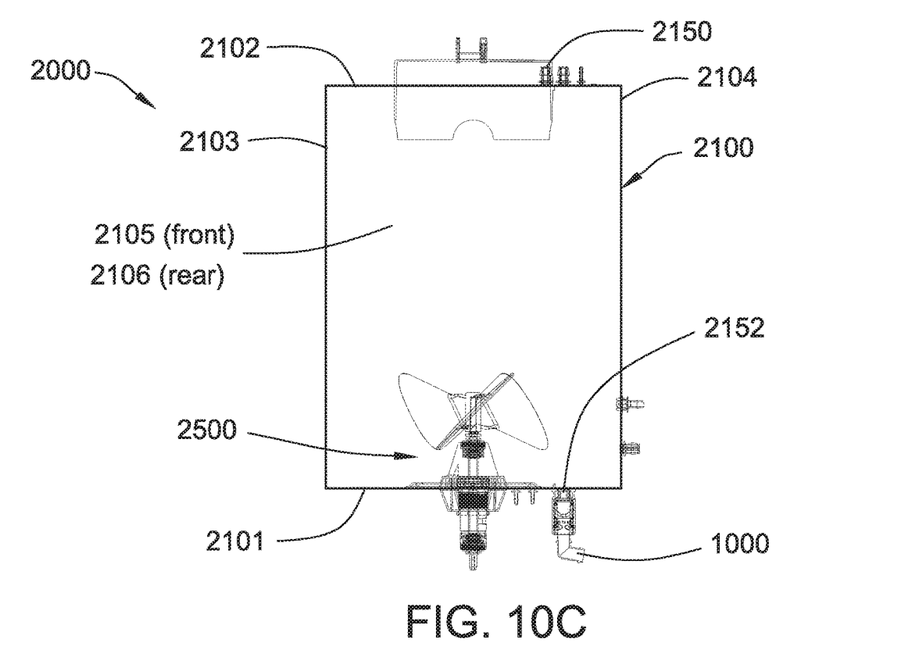

FIGS. 10A-10C illustrate various views of a system 2000 (such as a mixing system and/or a cell culture system) according to an embodiment of the invention, comprising a closed container 2100 (having an interior volume suitable for containing fluid) and a drain valve 1000, attached to a bottom wall of the container. The illustrated closed biocontainer or bioprocessing container 2100 comprises a bottom wall 2101, a top wall 2102, and opposing side walls 2103, 2104, and 2105, 2106, and includes a plurality of ports including at least one inlet port 2150 and, as shown in FIG. 10C, a drain port 2152 (having the drain valve mounted in the drain port, wherein the hollow drain inlet flange of the drain valve is attached to an inner surface of the bottom wall 2101), wherein an agitator 2500 is also mounted to the bottom wall 2101, the agitator comprising an rotatable impeller within the interior volume of the container, and agitator housing components mounted to inner and outer surfaces of the bottom wall.

The biocontainer (or bioprocessing container), which is flexible (e.g., plastic), can have any suitable form (e.g., cylindrical (having, for example, a single continuous side wall), square, or rectangular), and in FIGS. 10A-C is illustrated as having a generally rectangular cuboid form with a plurality of side walls.

Embodiments of the container can have any suitable number and locations of ports, for example, one or more of any of the following ports: a liquid inlet port, a gas inlet port, a gas outlet port, a powder inlet port, an acid/base inlet port, a probe port, and/or a sample port.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:
1. A drain valve with a rotatable outlet comprising:
   (a) a hollow drain inlet comprising:
      (i) a hollow body having a first open end and a second open end, and an exterior surface, the exterior sur- face further comprising at least one outwardly extending lug, the first end further comprising a flange including a central opening having an internal diameter;
(b) a valve member comprising closed first end and an open second end,
(i) the closed first end having an external diameter and a side wall including at least two outwardly extending projections providing a circumferential channel therebetween, and a resilient ring arranged in the circumferential channel,
(ii) a valve body having a base comprising a lower surface including a groove, and the open second end, the second end having an external diameter and the valve body including at least one aperture, and a base side wall including a circumferential channel,
wherein the external diameter of the closed first end is less than the external diameter of the second end and is at least equal to the internal diameter of the central opening of the flange, and,
wherein the valve member is arranged within the hollow body of the hollow drain inlet and is axially moveable toward the first and second open ends of the hollow body within the hollow drain inlet;
(c) the rotatable outlet comprising:
(i) a hollow member having a first open end comprising a lip arranged to fit within the groove in the lower surface of the base of the valve body wherein the valve member is not integral with the rotatable outlet, and a second open end, and an exterior surface, the exterior surface further comprising, arranged between the first open end and the second open end, at least two outwardly extending projections providing a circumferential channel therebetween, the hollow member forming an angle of at least about 20 degrees between the first end and the second end; and,
(d) a rotatable collar comprising:
(i) a shell body having a side wall having an internal surface including an inwardly projecting circumferential rib rotatably arranged in the circumferential channel of the rotatable outlet, the side wall further comprising at least one channel therethrough for receiving the outwardly extending lug of the drain inlet hollow body, the channel having corresponding channel walls, at least one terminal section including a closed end and a horizontal axis, and an angled section, angled from the horizontal axis;
wherein rotating the rotatable collar allows the outwardly extending lug of the hollow body to move along the shell side wall channel such that the valve member can move axially toward the first end of the hollow drain inlet to a first position closing the central opening of the flange, preventing fluid flow therethrough, and the valve member can move axially toward the second end of the hollow drain inlet to a second position allowing fluid flow through the hollow drain inlet and the rotatable outlet; and
wherein the rotatable outlet can be rotated independently of the rotatable collar without affecting the first position or the second position of the valve member.

2. A system for processing fluid comprising:
the drain valve with a rotatable outlet according to claim 1; and,
a closed container having an interior volume suitable for containing fluid, the container comprising a bottom wall, a top wall, at least one side wall, the at least one side wall being joined to the top wall and the bottom wall; and at least an inlet port, the drain valve being arranged in the bottom wall, wherein the hollow drain inlet flange of the drain valve is attached to the bottom wall of the container.

3. The drain valve of claim 1, wherein the closed first end of the valve member has a dome shape.

4. A system for processing fluid comprising:
the drain valve with a rotatable outlet according to claim 3; and,
a closed container having an interior volume suitable for containing fluid, the container comprising a bottom wall, a top wall, at least one side wall, at least one side wall being joined to the top wall and the bottom wall; and at least an inlet port, the drain valve being arranged in the bottom wall, wherein the hollow drain inlet flange of the drain valve is attached to the bottom wall of the container.

5. The drain valve of claim 1, wherein the at least one terminal section of the shell body side wall channel includes a lug retaining section having a cross-sectional area narrower than an outer diameter of the lug, the lug retaining section providing resistance as the lug passes through the narrower cross-sectional area.

6. The drain valve of claim 5, wherein the closed first end of the valve member has a dome shape.

7. A system for processing fluid comprising:
the drain valve with a rotatable outlet according to claim 5; and,
a closed container having an interior volume suitable for containing fluid, the container comprising a bottom wall, a top wall, at least one side wall, the at least one side wall being joined to the top wall and the bottom wall; and at least an inlet port, the drain valve being arranged in the bottom wall, wherein the hollow drain inlet flange of the drain valve is attached to the bottom wall of the container.

8. The drain valve of claim 1, wherein the at least one channel in the shell body side wall has two terminal sections, each including a closed end and a horizontal axis, and the angled section, angled from the horizontal axis, is arranged between the two terminal sections, the two terminal sections each including a lug retaining section having a cross-sectional area narrower than an outer diameter of the lug, the lug retaining section providing resistance as the lug passes through the narrower cross-sectional area.

9. The drain valve of claim 8, wherein the closed first end of the valve member has a dome shape.

10. A system for processing fluid comprising:
the drain valve with a rotatable outlet according to claim 8; and,
a closed container having an interior volume suitable for containing fluid, the container comprising a bottom wall, a top wall, at least one side wall, the at least one side wall being joined to the top wall and the bottom wall; and at least an inlet port, the drain valve being arranged in the bottom wall, wherein the hollow drain inlet flange of the drain valve is attached to the bottom wall of the container.

11. A method for operating a drain valve, the drain valve comprising
(a) a hollow drain inlet comprising:
(i) a hollow body having a first open end and a second open end, and an exterior surface, the exterior surface further comprising at least one outwardly extending lug, the first end further comprising a flange including a central opening having an internal diameter;

(b) a valve member comprising closed first end and an open second end,
   (i) the closed first end having an external diameter and a side wall including at least two outwardly extending projections providing a circumferential channel therebetween, and a resilient ring arranged in the circumferential channel,
   (ii) a valve body having a base comprising a lower surface including a groove, and the open second end, the second end having an external diameter and the valve body including at least one aperture, and a base side wall including a circumferential channel,
      wherein the external diameter of the closed first end is less than the external diameter of the second end and is at least equal to the internal diameter of the central opening of the flange, and,
      wherein the valve member is arranged within the hollow body of the hollow drain inlet and is axially moveable toward the first and second open ends of the hollow body within the hollow drain inlet;

(c) the rotatable outlet comprising:
   (i) a hollow member having a first open end comprising a lip arranged to fit within the groove in the lower surface of the base of the valve body wherein the valve member is not integral with the rotatable outlet, and a second open end, and an exterior surface, the exterior surface further comprising, arranged between the first open end and the second open end, at least two outwardly extending projections providing a circumferential channel therebetween, the hollow member forming an angle of at least about 20 degrees between the first end and the second end; and, (d) a rotatable collar comprising:
   (i) a shell body having a side wall having an internal surface including an inwardly projecting circumferential rib rotatably arranged in the circumferential channel of the rotatable outlet, the side wall further comprising at least one channel therethrough for receiving the outwardly extending lug of the drain inlet hollow body, the channel having corresponding channel walls, at least one terminal section including a closed end and a horizontal axis, and an angled section, angled from the horizontal axis;
      wherein rotating the rotatable collar allows the outwardly extending lug of the hollow body to move along the shell side wall channel such that the valve member can move axially toward the first end of the hollow drain inlet to a first position closing the central opening of the flange, preventing fluid flow therethrough, and the valve member can move axially toward the second end of the hollow drain inlet to a second position allowing fluid flow through the hollow drain inlet and the rotatable outlet; and
      wherein the rotatable outlet can be rotated independently of the rotatable collar without affecting the first position or the second position of the valve member;

the method comprising:
   rotating the rotatable collar and moving the outwardly extending lug of the hollow body along the shell side wall channel such that the valve member moves axially toward the first end of the hollow drain inlet to a first position closing the central opening of the flange, preventing fluid flow therethrough, and/or moving the valve member axially toward the second end of the hollow drain inlet to a second position allowing fluid flow through the hollow drain inlet and the rotatable outlet.

12. The method of claim 11, further including rotating the rotatable outlet independently of the rotatable collar.

* * * * *